US008019572B2

(12) United States Patent
Fink et al.

(10) Patent No.: US 8,019,572 B2
(45) Date of Patent: Sep. 13, 2011

(54) METHOD AND APPARATUS FOR EXPLORING BY WAVE PROPAGATION

(75) Inventors: Mathias Fink, Meudon (FR); Gabriel Montaldo, Paris (FR); Mickael Tanter, Bagneux (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 520 days.

(21) Appl. No.: 12/277,707

(22) Filed: Nov. 25, 2008

(65) Prior Publication Data
US 2010/0114533 A1 May 6, 2010

(30) Foreign Application Priority Data

Oct. 31, 2008 (FR) ...................... 08 57425

(51) Int. Cl.
*H03F 1/26* (2006.01)
(52) U.S. Cl. ..................................................... 702/189
(58) Field of Classification Search .................. 702/189, 702/182–185
See application file for complete search history.

(56) References Cited

U.S. PATENT DOCUMENTS

| 4,279,019 | A | * | 7/1981 | Heyser | 702/140 |
| 2005/0033170 | A1 | | 2/2005 | Angelsen et al. | |
| 2006/0241429 | A1 | | 10/2006 | Ustuner et al. | |

OTHER PUBLICATIONS

Karaman Met al: "Adaptive digital beamforming for phased array ultrasound imaging (medical US imaginq)", Ultrasonic Symposium, 9911208; 19911208-19911211 , Dec. 8, 1991, pp. 1207-1210, XP010094014.
International Search Report in Corresponding Application No. PCT/FR2009/052099 Dated Feb. 19, 2010.
C. Prada et al., "The iterative time reversal mirror: A solution to self-focusing in the pulse echo mode", J. Acoust. Soc. Am., Aug. 1991, pp. 1119-1129, vol. 90, No. 2, Acoustical Society of America.
Gabriel Montaldo et al., "Revisiting iterative time reversal processing: Application to detection of multiple targets", J. Acoust. Soc. Am., Feb. 2004, pp. 776-784, vol. 115, No. 2, Acoustical Society of America.
Raoul Mallart et al., "The van Cittert-Zernike theorem in pulse echo measurements", J. Acoust. Soc. Am., Nov. 1991, pp. 2718-2727, vol. 90, No. 5, Acoustical Society of America.
Mathieu Pernot et al., "Ultrasonic stars' for time-reversal focusing using induced cavitation bubbles", Applied Physics Letters, 2006, pp. 034102-1-034102-3, vol. 88, American Institute of Physics.
S.W. Flax et al., "Phase-Aberration Correction Using Signals From Point Reflectors and Diffuse Scatterers: Basic Principles", IEEE Transactions on Ultrasonics, Ferroelectrics, and Frequency Control, Nov. 1988, pp. 758-767, vol. 35, No. 6, IEEE.

* cited by examiner

*Primary Examiner* — Edward Raymond
(74) *Attorney, Agent, or Firm* — Young & Thompson

(57) ABSTRACT

A method of exploring by wave propagation, in which method an incident wave is emitted a plurality of times towards the same target zone ($r_0$) in a diffusing medium, and then the backscattered signals generated by the waves are averaged.

16 Claims, 3 Drawing Sheets

METHOD AND APPARATUS FOR EXPLORING BY WAVE PROPAGATION

FIELD OF THE INVENTION

The present invention relates to methods and devices for exploring by wave propagation.

More particularly, the invention relates to a method of exploring by wave propagation, which method comprises:

(a) a measurement step including a plurality of emissions (a1) during which a set of transducers i (i.e. all or some of the transducers in the set) are caused to emit incident waves into a diffusing medium, and a plurality of receptions (a2) during which the set of transducers (i.e. all or some of the transducers in the set) are caused to pick up signals representative of the waves reverberated by the medium from each incident wave; and (b) a processing step during which the picked-up signals are processed.

It should be noted that each of the above-mentioned transducers can be any device capable of transforming an electrical signal into a wave, regardless of the type of the wave.

The above-mentioned processing step makes it possible, for example, to measure a parameter that is characteristic of the medium, and/or to detect a remarkable point of the medium, and/or to form an image of the medium, and/or to determine impulse responses of the medium then making it possible to focus a signal at predetermined locations of the medium (e.g. for communications, therapeutic treatment, or other purposes).

BACKGROUND OF THE INVENTION

Methods of this type are usable in particular in detection and imaging systems, such as, for example, sonar systems, radars, echographs, adaptive optics imaging systems, etc. for the purposes of medical imaging, therapeutic treatment, non-destructive testing of materials, in seismology and subsoil imaging, etc.

Such known methods suffer from having major implementation difficulties when the medium is an aberrating medium, in particular due to it being heterogeneous, because it is then difficult to focus the waves effectively whether in emission or in reception.

Various methods have already been proposed for correcting the distortions introduced by the heterogeneities of the medium under imaging. Some of those methods are based on the use of a (reflective) bright point in the focusing zone that makes it possible to correct the distortions—see, in particular Prada et al. [*"The iterative time reversal process: A solution to self-focusing in the pulse echo mode"*, J. Acoust. Soc. Am. 90, 1119-1129, 1991].

In the more general case, unfortunately such a shiny spot is unavailable. Therefore, methods have been developed by Mallart et al. [*"The van Cittert-Zernike theorem in pulse echo measurements"*, J. Acoustical Soc. Am., Vol 90, Issue 5, pp. 2718-2727, 1991] for using the coherence of the waves back-scattered by the medium, but the lack of robustness of those methods prevents them from being implemented industrially.

SUMMARY OF THE INVENTION

A particular object of the present invention is to mitigate those drawbacks.

To this end, according to the invention, during the processing step, consideration is given to a plurality of sets $k$ of reverberated signals $B_k(i, t)$, each of which comes substantially from a point $r_k$ belonging to the same isoplanatic zone $ZI(r_0)$ that is common to said sets $k$ of signals and that itself relates to a point $r_0$ of the medium, the points $r_k$ being either different from one another regardless of the medium, or coinciding with the point $r_0$ when the medium includes diffusers having random motion;

the reverberated signals $B_k(i, t)$ of the sets $k$ are re-positioned in time if the points $r_k$ are different from one another in order to obtain corrected signals $B0_k(i, t) = B_k(i, t - G_i(r_k))$, where the values $G_i(r_k)$ are delays such that, by causing the transducers i to emit signals $e_k(i, t) = e_0(i, t + G_i(r_k))$, the incident wave focuses substantially at the point $r_k$, the signals $e_0(i, t)$ being reference signals such that, by causing the transducers i to emit said reference signals $e_0(i, t)$, the incident wave focuses substantially at the point $r_0$;

the signals $B0_k(i, t) = B_k(i, t - G_i(r_k))$ are put into phase and averaged (it should be noted that when each point $r_k$ coincides with $r_0$, $G_i(r_k) = 0$, and thus $B0_k(i, t) = B_k(i, t)$) so as to obtain average signals $$Bf(i, t) = \sum_k A_k B0_k(i, t - c_k)$$

where the values $c_k$ are delays making it possible to put the signals $B0_k$ into phase, and the values $A_k$ are weighting coefficients (optionally, all of the coefficients $A_k$ can be equal to 1).

By means of these features, it is possible to eliminate the spatially incoherent variations of the picked-up signal due to the aberrations of the medium, so that it is thus possible to be unaffected by the distortions generated by the heterogeneities of the medium, even in media that are highly aberrating (e.g. the skull in ultrasound imaging or ultrasound treatment, or indeed the layers of fat and of muscles in ultrasound imaging or ultrasound treatment of the abdomen).

The method of the invention is easy to implement, even in pre-existing system, and it is particularly robust.

It should be noted that the reverberated signals $B_k(i, t)$ are not necessarily physically reverberated and do not necessarily physically come from the points $r_k$: said signals can be:

either physically picked up from incident waves focused respectively at the points $r_k$, in which case they are indeed physically reverberated and they do indeed physically come from the points $r_k$;

or else synthesized from incident waves that are not focused at the points $r_k$, in which case the synthetic signals are not physically reverberated from the points $r_k$ but rather they reproduce what signals physically reverberated from the points $r_k$ would be like.

In various implementations of the method of the invention, it is optionally possible also to use one or more of the following features:

each set $k$ of signals corresponds to an emission $k$ focused at the point $r_k$, and, during each emission $k$, signals $e_k(i, t) = e_0(i, t + G_i(r_k))$ are emitted;

the delays $G_i(r_k)$ are such that, by causing signals $e_k(i, t) = e_0(i, t + G_i(r_k))$ to be emitted by the transducers i, the incident wave focuses at the point $r_k$, assuming that the medium is homogeneous;

the reference signals $e_0(i, t)$ are determined as if the medium were homogeneous;

the delay $c_k$ is computed by comparison between the signals $B0_k(i, t)$ and the signal $e_0(i, t)$;

the delay $c_k$ is computed by comparison between the signals $B0_k(i, t)$;

the measurement and processing steps are implemented in a plurality of successive iterations j for the same isoplanatic zone $ZI(r_0)$ so as to obtain, at each iteration, an average signal $Bf_j(i, t)$, the signal $e0(i, t)$ used for the emission (a1) of each new iteration j subsequent to the initial iteration 1 being determined on the basis of an estimation of a time reversal $Bf_{j-1}(i, -t)$ of the average signal $Bf_{j-1}(i, t)$ determined in the step j−1;

said estimation of the time reversal is determined on the basis of a wavefront of the time reversal $Bf_{j-1}(i, -t)$;

the reference signals $e_0(i, t)$ of the initial iteration j=1, are determined as if the medium were homogeneous;

the points $r_k$ all coincide with the point $r_0$, the delays $G_i(r_k)$ being equal to 0, and the medium including diffusers having random motion;

the reverberated signals $B_k(i, t)$ are constructed by a synthesis method on the basis of the emissions and receptions made during the measurement step;

a plurality of average signals $Bf(i, t)$ are determined that relate to different points $r_0$ of the medium, and said mean signals $Bf(i, t)$ are used to build an image of the medium;

the average signal $Bf(i, t)$ is used to compute a parameter that is specific to the medium;

said parameter is the wave propagation speed; and said waves are selected from among ultrasonic waves, mechanical waves (other than ultrasound waves), and electromagnetic waves.

In addition, the invention also provides apparatus for implementing a method of exploring as defined above, said apparatus comprising a set of transducers i suitable for emitting an incident wave into a diffusing medium, and for picking up signals representative of a reflected wave reverberated by the medium from the incident wave, the apparatus further comprising control means suitable for causing said set of transducers to take at least one measurement including a plurality of emissions (a1) during which the set of transducers i are caused to emit incident waves into the medium, and a plurality of receptions (a2) during which the signals representative of the reflected waves reverberated by the medium from each incident wave are picked up; and the device further comprising processing means adapted to performing a processing step (b) during which consideration is given to a plurality of sets k of reverberated signals $B_k(i, t)$, each of which comes substantially from a point $r_k$ belonging to the same isoplanatic zone $ZI(r_0)$ that is common to said sets k of signals and that itself relates to a point $r_0$ of the medium, the points $r_k$ being either different from one another regardless of the medium, or coinciding with the point $r_0$ when the medium includes diffusers having random motion;

said processing means being adapted to:

re-position in time the reverberated signals $B_k(i, t)$ of the sets k if the points $r_k$ are different from one another in order to obtain corrected signals $B0_k(i, t)=B_k(i, t-G_i(r_k))$, where the values $G_i(r_k)$ are delays such that, by causing the transducers i to emit signals $e_k(i, t)=e_0(i, t+G_i(r_k))$, the incident wave focuses substantially at the point $r_k$, the signals $e_0(i, t)$ being reference signals such that, by causing the transducers i to emit said reference signals $e_0(i, t)$, the incident wave focuses substantially at the point $r_0$; and to put into phase and average the signals $B0_k(i, t)=B_k(i, t-G_i(r_k))$ so as to obtain average signals $$Bf(i, t) = \sum_k A_k B0_k(i, t - c_k)$$

where the values $c_k$ are delays making it possible to put the signals $B0_k$ into phase, and the values $A_k$ are weighting coefficients.

BRIEF DESCRIPTION OF THE DRAWINGS

Other characteristics and advantages of the invention appear from the following description of embodiments and implementations thereof, given by way of non-limiting example and with reference to the accompanying drawings.

In the drawings.

DETAILED DESCRIPTION

In the various figures, like references designate elements that are identical or similar.

Figure 1:
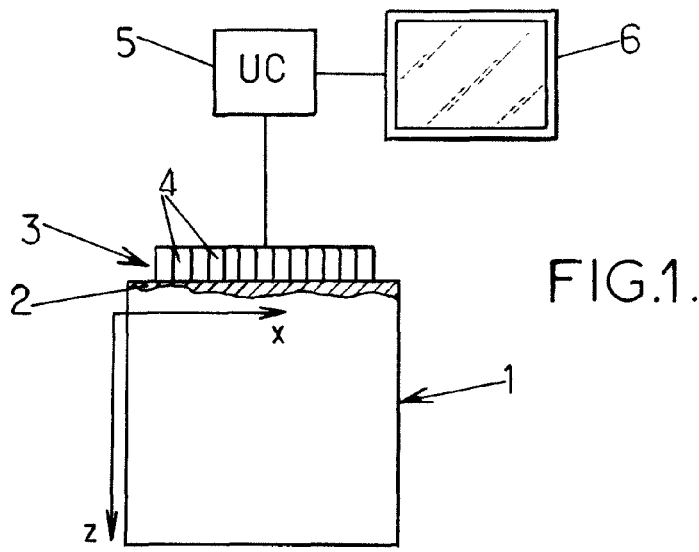
FIG. 1 is a diagrammatic view of an embodiment of apparatus for implementing a method of the invention.

FIG. 1 shows an example of apparatus suitable for exploring a medium 1 by emission and reception of waves. The invention is described below more particularly when the waves in question are ultrasonic compression waves (e.g. of frequencies lying in the range 2 megahertz (MHz) to 4 MHz). However, it should be noted that the invention is also applicable to waves of any type, e.g. to mechanical waves other than ultrasonic compression waves, electromagnetic waves, or other waves.

The medium 1 is diffusing for the waves in question, and more particularly it contains diffusers 2 distributed randomly and capable of reflecting the waves emitted into the medium 1.

The medium 1 in question can, for example, be a portion of the human body, and the diffusers can, in particular, be small-size non-resolved particles that are contained in the medium 1 (in echography, such diffusers generate "speckle" images). Naturally, the medium 1 to be explored may be otherwise, e.g. a portion of an industrial article whose structure it is desired to test non-destructively.

In the example under consideration, the medium 1 also has an aberrating layer 2. An example of such an aberrating layer is constituted by the skull in ultrasound imaging of the brain, or by layers of fat and of muscles in ultrasound imaging of the abdomen, but more generally, it can be any layer that is heterogeneous relative to the remainder of the medium 1.

The exploring apparatus shown in FIG. 1 includes a set 3 of transducers 4, e.g. a linear array of ultrasonic piezoelectric transducers that can conventionally be in the form of a rigid strip put into contact with the medium 1 (and more particularly with the aberrating layer 2 in the example under consideration). In the example shown, said strip extends along an axis x and makes it possible to explore the medium 1 in a plane (x, z), where z is an axis perpendicular to x and extending in the depth of the medium 1.

The array 3 of transducers comprises a number N of transducers, it being possible, for example, for N to lie in the range 100 to 500. For example, it is possible to use a strip of about one hundred transducers 4, each having a width of about 0.39 mm. It should be noted that, in this example, the transducers 4 are ultrasonic transducers capable of transforming an electrical signal into ultrasonic compression waves or vice versa, but, in the meaning of the present patent, the term "transducer" is used more generally to mean any device capable of transforming an electrical signal into a wave of any type whatsoever (mechanical wave, electromagnetic wave, optical wave, etc.) and vice versa.

Each transducer 4 of the array 3 can be controlled individually by a central processing unit 5 (UC) including, for example, digital signal-processing means, it being possible, for example, for the central processing unit 5 to be adapted to present an image of the medium 1 on a screen 6.

For exploring the medium 1, the central processing unit 5 sends to the transducers 4 electrical signals that are transformed by said transducers into waves emitted into the medium 1, which waves are, in this example, ultrasonic compression waves, and said waves are reflected partially by the diffusers contained in the medium. Some of the waves diffused (or echoes) thus return towards the transducers 4 that pick them up and that transform them into reception electrical signals that are then processed by the central processing unit 5.

The method of the invention makes provision to correct the effects of the aberrating layer 2, by emitting towards each point $r_0$ under study of the medium 1, a group of n incident waves focused towards said point or towards the vicinity thereof, where n is an integer that is preferably greater than 5 and that, for example, lies in the range 5 to 20, and in particular in the range 10 to 15.

Figure 2:
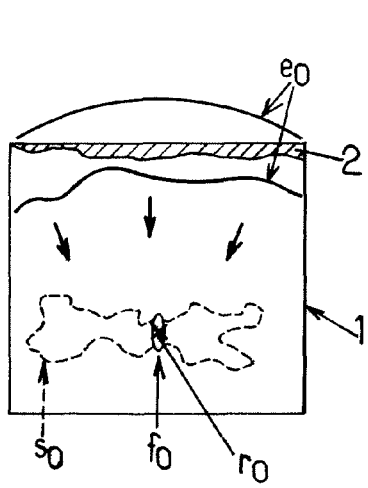
FIG. 2 is a diagram showing the successive wavefronts of an incident acoustic wave $e_1$ focused on a point $X_1$ of the medium under study.

FIG. 2 diagrammatically shows the emission of a first incident wave $e_0(x, z, t)$ focused towards a point $r_0$ of the medium 1. This incident wave is generated by causing each transducer i of the array 3 to emit a signal $e_0(i, t)$ that is determined by applying a cylindrical delay relationship to a reference signal. Conventionally, this delay relationship is determined so as to compensate for the differences in pathlength between each transducer i and the focal point $r_0$, by assuming a priori that there is no aberration (wrongly, and as any conventional echograph does).

The quality of focusing is however strongly degraded by the heterogeneities introduced by the aberrating layer 2, resulting in a considerable deformation of the wavefront after it has passed through the aberrating layer 2, as shown in FIG. 2. In particular, the level of secondary lobes of the focal spot is high. At the focal point $r_0$, the wave can be broken down into the sum of two terms: the focusing signal $f_0(x, z, t)$ at the focal point $r_0$ (i.e. the signal that would be obtained in the absence of any aberrating layer), and the signal $s_0(x, z, t)$ corresponding to the secondary lobes (to the "imperfections" of the focusing).

Figure 3:
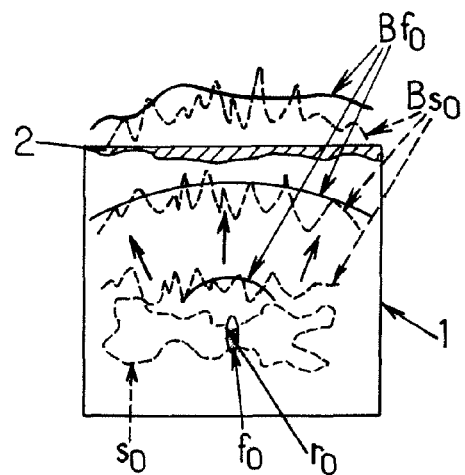
FIGS. 3 and 4 are views similar to FIG. 2, showing the successive wavefronts of two components ($Bf_1$ & $Bs_1$ for FIG. 3, and $Bf_2$ & $Bs_2$ for FIG. 4) of the wave backscattered by the medium, following two successive emissions of the same incident wave e1 focused on the same point $X_1$.
Figure 4:
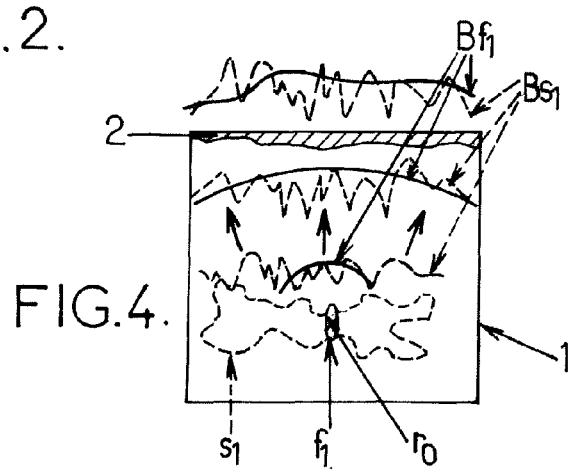

As shown in FIG. 3, the backscattered signals received on the array of transducers can be expressed in the following form:

$$B_0(x,t) = Bf_0(x,z,t) + Bs_0(x,z,t)$$

where $Bf_0(x,t)$ corresponds to the backscattering of the focusing signal, and $Bs_0(x,t)$ corresponds to the backscattering of the lobes describing the focusing degradation.

As stated by the van Cittert-Zernike theorem [see, in particular: R. Mallart and M. Fink, "*The van Cittert-Zernike theorem in pulse echo measurements*", J. Acoustical Soc. Am., Vol 90, Issue 5, pp. 2718-2727, 1991], the spatial coherence of the signals backscattered by a set of diffusers distributed randomly in space is inversely proportional to the size of the source, so that the signal backscattered by the focal spot (equivalent to a small source) is a coherent signal, and the signals backscattered by lobes (constituting an extended source) is an incoherent signal.

If the positions of the diffusers contained in the medium 1 change randomly between two ultrasonic wave launches by the array 3 of transducers (e.g. if the medium 1 is a living medium having a certain amount of mobility or a fluid medium in motion, e.g. blood), subsequent emission of another incident wave $e_1(x, z, t)$ of waveform identical to the first incident wave $e_0(x, z, t)$, results in new backscattered signals being formed $B_1(x,t) = Bf_1(x,t) + Bs_1(x,t)$.

Figure 5:
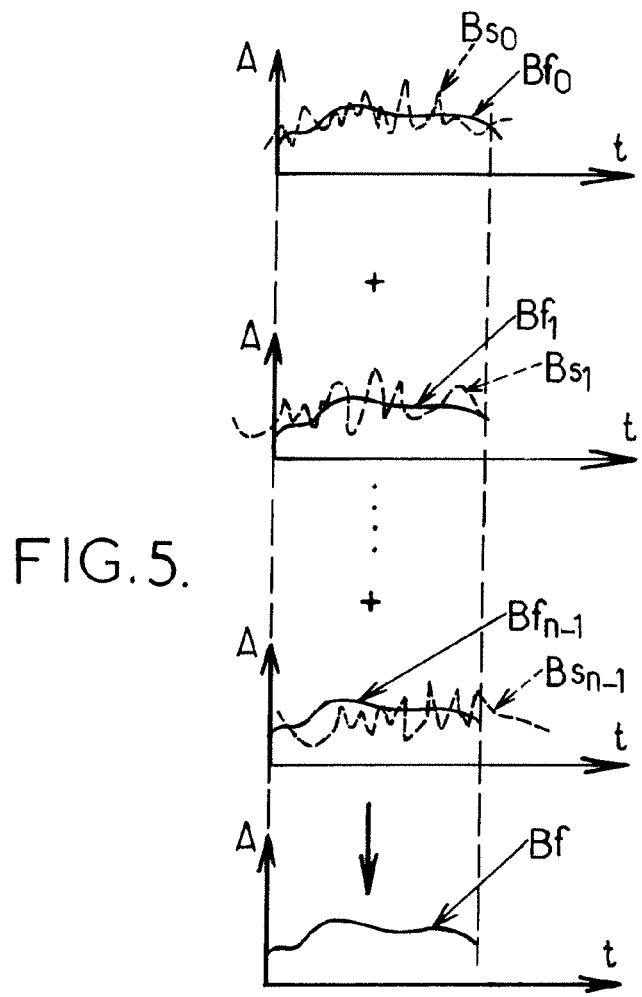
FIG. 5 diagrammatically shows the averaging processing that is applied to a group of n signals received by each transducer i after a group of n launches of waves focused on the same point $X_1$.
Figure 6:
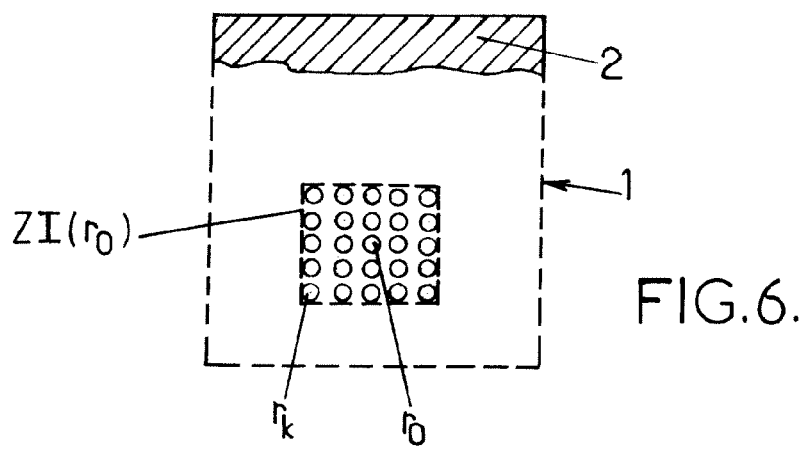
FIG. 6 is an enlarged view showing various points $r_k$ towards which the incident wave can be focused successively within a small zone referred to as an "isoplanatic zone" around a central point $X_1$ so as to obtain a group of picked-up signals to which the averaging processing shown diagrammatically in FIG. 5 can be applied.

It is thus possible to effect a group of emissions comprising n launches of incident waves $e_0(x, z, t)$, $e_1(x, z, t)$, ... $e_k(x, z, t)$, ... $e_{n-1}(x, z, t)$ focused towards the target point $r_0$, and then to average the various backscattered signals $B_0(x, z, t)$, $B_1(x, z, t)$, ... $B_k(x, z, t)$, ... $B_{n-1}(x, z, t)$ (forming the same group of receptions corresponding to the above-mentioned group of n emissions), as shown in FIG. 5. When computing this average, the coherent parts of the signals add constructively, but the incoherent parts are summed destructively and are finally eliminated during computation of the average:

$$\frac{1}{n}\sum_k Bs_k(x, z, t) \to 0: \quad Bf = \frac{1}{n}\sum_k B_k(x, z, t) \cong \frac{1}{n}\sum_k Bf_k(x, z, t).$$

It should be noted that the above-mentioned average could be an average that is weighted by using weighting coefficients $A_k$.

In practice, the successive backscattered signals $Bf_k(i, t)$ picked up after each launch k, by each transducer i of the array 3, are averaged. The resulting signal $Bf(i, t)$ obtained by averaging for each transducer i, is representative of the above-mentioned coherent signal Bf:

$$Bf(i, t) = \frac{1}{n}\sum_k B_k(i, t) \cong \frac{1}{n}\sum_k Bf_k(i, t).$$

This process can be repeated for a plurality of target points $r_0$ in the medium 1. For uses in imaging, it is thus possible to repeat the process for a matrix of target points $r_0$ covering the entire zone to be imaged.

The coherent signals $Bf(i, t)$ computed by averaging for each point $r_0$ of the medium 1 can then be used conventionally either for constructing an image of the medium 1, or for making it possible to emit subsequently a wave that is focused precisely at a particular point of the medium (e.g. for therapeutic or other purposes), or indeed for computing a parameter of the medium (e.g. the propagation speed of the waves in question, in particular of the ultrasonic compression waves in the particular example described herein).

The above-described method can be further improved in two respects:

zone averaging: in most uses, the medium does not change, and it is not possible to have different time configurations of the random medium: in which case, it is possible to perform averaging per zone, by using various space configurations of the random medium obtained by focusing successively the incident waves of the various emissions of the same group of emissions at a plurality of points situated in a small zone referred to as an "isoplanatic" zone, around the target point $r_0$ of said group of emissions; and re-phasing: in particular when the medium changes, the waves $f_k(x, z, t)$ and $f_{k'}(x, z, t)$ of the same group of emissions are not in phase: the signals picked up must then preferably be put back into phase prior to averaging.

Zone Averaging

In a static medium, it is impossible to obtain different random configurations of backscattered signals in the same reception group (corresponding to the same point $r_0$ of the medium 1), by using incident waves that are focused exactly on the point $r_0$.

In order to solve this problem and in order to be able to determine the above-mentioned average signals Bf(i, t) for each of the target points $r_0$ under exploration, the incident waves are focused at different points $r_k$ of the medium around the target focusing point in question $r_0(x_0, z_0)$, within a small zone $ZI(r_0)$ surrounding the target point in question $r_0(x_0, z_0)$.

This small zone $ZI(r_0)$, referred to as an "isoplanatic" zone, is such that the incident wave can be focused effectively at $r_k$ merely by angulation (i.e. by applying delays to the various transducers 4) relative to the incident wave focused at $r_0$. More precisely, it is possible to define the isoplanatic zone $ZI(r_0)$ by the fact that the backscattered wavefronts coming from any point of said zone are identical to within about one quarter of a wavelength, ignoring the time offset related to the gap between the points in question of the isoplanatic zone.

It should be noted that in the above-described case in which all of the incident waves of the same group of emissions are focused exactly at the same point $r_0$, all of these incident waves are, even more so, focused in the isoplanatic zone $ZI(r_0)$ attached to this point $r_0$.

In the case considered herein of focusing at a plurality of points $r_k$, the n emissions of the same group of emissions are thus focused respectively on $r_0$ and on other points $r_k$ of the isoplanatic zone $ZI(r_0)$, i.e. n points in total (where n can preferably be greater than 5 and, for example, lie in the range 5 to 20, in particular in the range 10 to 15, as in the above-described example). The signals $e_k(i, t)$ emitted by the transducers 1 of the array 3 are expressed in the form: $e_k(i, t) = e_0(i, t+G_i(r_k))$, where $G_i(r_k)$ is a delay applied to the signal of the transducer i relative to the above-mentioned reference signal $e_0(i, t)$ ($e_0(i, t)$ is the signal making it possible to focus at $r_0$) so that the incident wave focuses substantially at $r_k$. This delay $G_i(r_k)$ can, for example, be determined as if the medium 1 were homogeneous.

During the various launches of incident waves towards the isoplanatic zone $ZI(r_0)$, when focusing at the point $r_0(x_0, z_0)$, the backscattered signal is $B_0(x,t)=Bf_0(x,t)+Bs_0(x,t)$ as noted above.

Conversely, when focusing the incident wave at a point $r_k$ distinct from $r_0$ and belonging to the isoplanatic zone $ZI(r_0)$ [this point having, for example, as its coordinates $r_k(x_0+\Delta x, z_0)$ if it is at the same depth $z_0$ as $r_0$], a different configuration of the backscattering is obtained because a different zone of diffusers placed randomly in the direction x:$B_k(x,t)=Bf_k(x+\Delta x,t)+Bs_k(x+\Delta x,t)$ is illuminated.

On the basis of this group of n emissions, it is possible, as in the preceding case, to obtain a group of n receptions corresponding to the isoplanatic zone $ZI(r_0)$, these n receptions resulting in i*n picked-up signals $B_k(i, t)$.

These signals are firstly re-positioned in time between themselves so as to correct the phase shift introduced by the fact that the incident waves are focused at points $r_k$ that are slightly different. To this end, corrected signals $B0_k(i, t)=B_k(i, t-G_i(r_k))$ are computed. It should be noted that this formula is exactly the same as in the preceding case, i.e. when always focusing at the same point $r_0$, because $r_k=r_0$, $G_i(r_k)=0$ and $B0_k(i, t)=B_k(i, t)$ are then satisfied.

Finally, the corrected signals $B0_k(i, t)$ are put into phase and averaged so as to obtain average signals $$Bf(i, t) = \sum_k A_k B0_k(i, t - c_k)$$

where the values $c_k$ are delays making it possible to put into phase the signals $B0_k$ and the weighting coefficients $A_k$ (possibly all equal to 1). The delays $C_k$ making the re-phasing possible are determined below in the "Re-phasing" portion.

As explained above, this process can be repeated for a plurality of target points $r_0$ so as to cover the entire zone to be explored of the medium 1.

Re-Phasing

Between two backscattered signals $B_k(x, z, t)$ and $B_{k'}(x, z, t)$ coming from two different launches of the same group corresponding to two different configurations of the diffusers (i.e. to two different random states of the diffusers), the coherent signals $Bf_k(x, z, t)$ and $Bf_{k'}(x, z, t)$ are practically the same, but a phase difference can exist between the two signals even after time re-positioning, e.g. due to the fact that the medium has changed between two launches or merely due to the fact that the time re-positioning does not make it possible to re-phase two backscattered signals entirely after focusing at two distinct points, in view of the heterogeneity of the medium.

It is then useful to re-phase the signals prior to averaging. This re-phasing operation can be performed by various methods, in particular by methods of comparison between backscattered signals and by methods of comparison with the reference signal $e_0$.

For comparison between signals, it is possible to compute, for example, a time correlation between $B0_k$ and $B0_{k'}$, e.g. between $B0_k$ and $B0_0$:

$$Ck(\tau)=\int B0_k(i,t)B0_0(i,t-\tau)dt$$

$Ck(\tau)$ has a maximum for $\tau=c_k$, which is the value of the phase shift $c_k$ between $B0_k(i, t)$ and $B0_0(i, t)$, which phase shift it is necessary to apply to each corrected signal $B0_k(i, t)$ in order to re-phase all of the signals $B0_k$ relative to one another.

For comparison with the reference signal $e_0$, it is possible, for example, to compute a time correlation $C(\tau)$ between the time reversal $B0_k(i, -t)$ and $e_0(i, t)$ ($Ck(\tau)=\int B0_k(i, -t)e_0(i, t-\tau)dt$), this formula having a maximum for $\tau=c_k$ which is the delay to be applied to each corrected signal $B0_k(i, t)$ for re-phasing all of the signals $B0_k(i, t)$ relative to one another.

Iterative Procedure

Once the coherent signals Bf(i, t) corresponding to each target point $r_0$ of the medium 1 have been obtained, it is possible to construct another emission that focuses on the point $r_0$ with better focusing than the initial focusing. This other signal can be formed by time-reversing the signal Bf(i, t): $e_0(i, t)=Bf(i, -t)$ is then taken as the reference signal because this signal focuses at $r_0$.

It is then possible to reiterate the above-mentioned steps for measurement (emission/reception) and for processing of the received signals in a plurality of successive iterations j for each isoplanatic zone $ZI(r_0)$ so as to obtain, at each iteration, an average signal $Bf_j(i, t)$ (i.e. the above-mentioned average signal Bf, computed for the iteration j), the signal $e_0(i, t)$ used for the emission (a1) of each new iteration j subsequent to the initial iteration (j=1) being determined on the basis of an estimation of a time reversal $Bf_{j-1}(i, -t)$ of the average signal $Bf_{j-1}(i, t)$ determined in step j−1.

At the end of a few iterations, generally in the range 3 iterations to 4 iterations, it is possible to converge towards a stable value for the signals Bf(i, t).

It should be noted that, during this iterative process, a mere approximation of the time reversal $Bf_{j-1}(i, -t)$ is generally determined on going over from iteration j−1 to iteration j, if only because of operating on samples of the signals.

This approximation can optionally merely be the wavefront of the time reversal $Bf_{j-1}(i, -t)$. Thus, when only transducers 4 of the pulser type are available, it is possible to approximate Bf(x,−t) merely by a delay and amplitude relationship $Bf(x,-t) \approx A(x)P(t-r(t))=e_2(x,t)$ where A(x) is the amplitude relationship, r(t) is the delay relationship, and P(t) is the pulse waveform that is identical on each path.

Use of Synthetic Signals

In all of the above-mentioned variants, it is optionally possible to emit incident waves that are not focused on the point(s) $r_k$. In which case, it is possible to construct, a posteriori, reverberated signals $B_k(i, t)$ using conventional synthesis methods on the basis of emissions and receptions made during the measurement step (e.g. by linear combination of signals picked up on the basis of the non-focused incident waves), as if said signals $B_k(i, t)$ had been picked up following an emission of a wave focused at $r_k$. These synthesized signals $B_k(i, t)$ are then processed as explained above.

Application to Correction of Aberrations in Echographic Imaging

Figure 8:
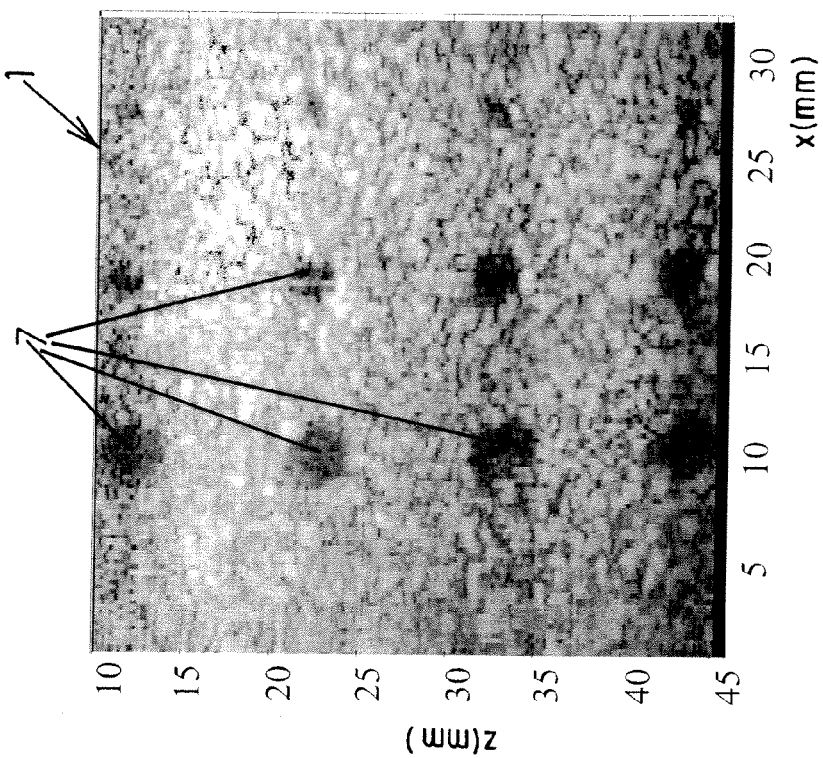
FIGS. 7 and 8 are examples of images of the medium of FIG. 1, obtained respectively by conventional echography and by the method of the invention.
Figure 7:
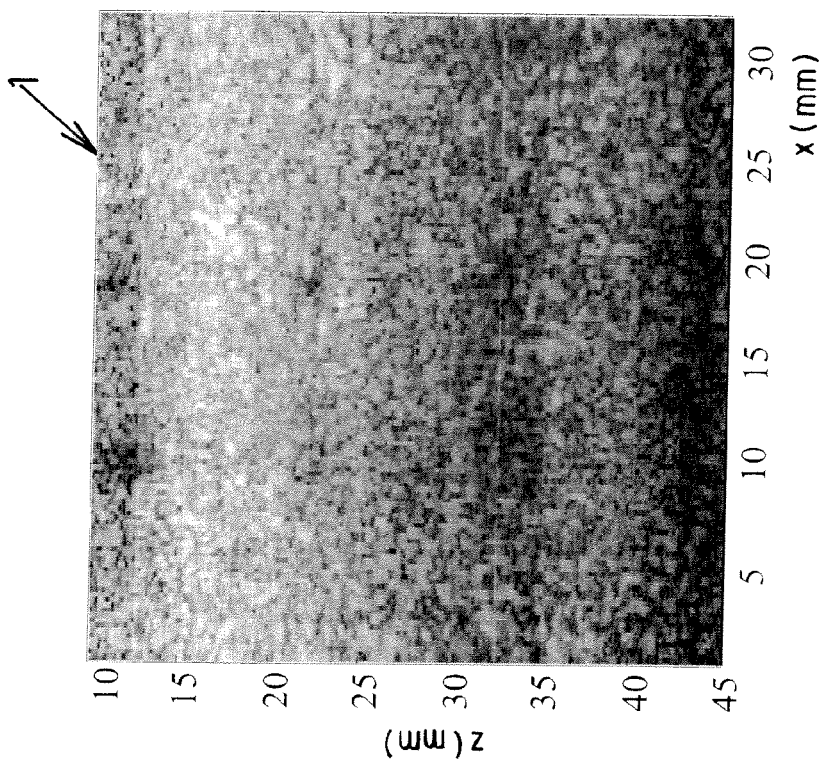

FIGS. 7 and 8 respectively show two echographic images of a medium 1 constituted by a block of gelatin containing a multitude of small diffusers (Agar powder) that are much smaller than the wavelength. An aberrating medium having a thickness of 3 mm and of irregular shape is placed between the array of transducers and the medium. It generates large phase variations over the ultrasonic beams ($>2\pi$).

In FIG. 7, the image is obtained by conventional echography techniques (formation of paths) and it does not make it possible to distinguish any detail. In FIG. 7, the image is obtained by implementing the method of the invention iteratively. After 3 to 4 iterations, the coherent signals obtained by averaging are representative of the Green functions of the medium and they make it possible to obtain an image of much superior quality. In the corrected image, it is thus possible to see clearly the anechoic zones 7 that are invisible in the standard image.

Application to Computing the Average Wave Propagation Speed in a Homogeneous or Stratified Medium Consideration is given below to a homogenous medium of unknown wave propagation speed. It is possible to compute said speed by using the coherent contribution of the backscattered waves that is obtained using our innovative technique. In a homogeneous medium, the coherent portion of the backscattered signal coming from the point $r_0$ corresponds to:

$$Bf(x, t) = \frac{1}{r}P(t - r/c)$$

where $$r^2 = (x - x_0)^2 + z_0^2$$

The wave propagation speed c can be deduced by causing the averaged picked-up signals Bf(i, t) to coincide with an analytical curve coming from a propagation model. This application can easily be extended to the case of stratified heterogeneous media.

The invention claimed is:

1. A method of exploring by wave propagation, which method comprises:
    (a) a measurement step including a plurality of emissions (a1) during which a set of transducers i are caused to emit incident waves into a diffusing medium, and a plurality of receptions (a2) during which the set of transducers are caused to pick up signals representative of the waves reverberated by the medium from each incident wave; and
    (b) a processing step during which the picked-up signals are processed;
    wherein, during the processing step, consideration is given to a plurality of sets k of reverberated signals $B_k(i, t)$, each of which comes substantially from a point $r_k$ belonging to the same isoplanatic zone $ZI(r_0)$ that is common to said sets k of signals and that itself relatives to a point $r_0$ of the medium, the points $r_k$ being either different from one another regardless of the medium, or coinciding with the point $r_0$ when the medium includes diffusers having random motion;
    wherein the reverberated signals $B_k(i, t)$ of the sets k are re-positioned in time if the points $r_k$ are different from one another in order to obtain corrected signals $B0_k(i, t)=B_k(i, t-G_i(r_k))$, where the values $G_i(r_k)$ are delays such that, by causing the transducers i to emit signals $e_k(i, t)=e_0(i, t+G_i(r_k))$, the incident wave focuses substantially at the point $r_k$, the signals $e_0(i, t)$ being reference signals such that, by causing the transducers i to emit said reference signals $e_0(i, t)$, the incident wave focuses substantially at the point $r_0$;
    and wherein the signals $B0_k(i, t)=B_k(i, t-G_i(r_k))$ are put into phase and averaged so as to obtain average signals $$Bf(i, t) = \sum_k A_k B0_k(i, t - c_k)$$

where the values $c_k$ are delays making it possible to put the signals $B0_k$ into phase, and the values $A_k$ are weighting coefficients.

2. A method according to claim 1, in which each set k of signals corresponds to an emission k focused at the point $r_k$, and, during each emission k, signals $\bar{e}_k(i, t)=e_0(i, t+G_i(r_k))$ are emitted.

3. A method according to claim 1, in which the delays $G_i(r_k)$ are such that, by causing signals $e_k(i, t)=e_0(i, t+G_i(r_k))$ to be emitted by the transducers i, the incident wave focuses at the point $r_k$, assuming that the medium is homogeneous.

4. A method according to claim 1, in which the reference signals $e_0(i, t)$ are determined as if the medium were homogeneous.

5. A method according to claim 1, in which the delay $c_k$ is computed by comparison between the signals $B0_k(i, t)$ and the signal $e_0(i, t)$.

6. A method according to claim 1, in which the delay $c_k$ is computed by comparison between the signals $B0_k(i, t)$.

7. A method according to claim 2, in which the measurement and processing steps are implemented in a plurality of successive iterations j for the same isoplanatic zone $ZI(r_0)$ so as to obtain, at each iteration, an average signal $Bf_j(i, t)$, the signal $e0(i, t)$ used for the emission (a1) of each new iteration j subsequent to the initial iteration 1 being determined on the basis of an estimation of a time reversal $Bf_{j-1}(i, -t)$ of the average signal $Bf_{j-1}(i, t)$ determined in the step j-1.

8. A method according to claim 7, in which said estimation of the time reversal is determined on the basis of a wavefront of the time reversal $Bf_{j-1}(i, -t)$.

9. A method according to claim 7, in which the reference signals $e_0(i, t)$ of the initial iteration j=1, are determined as if the medium were homogeneous.

10. A method according to claim 1, in which the points $r_k$ all coincide with the point $r_0$, the delays $G_i(r_k)$ being equal to 0, and the medium including diffusers having random motion.

11. A method according to claim 1, in which the reverberated signals $B_k(i, t)$ are constructed by a synthesis method on the basis of the emissions and receptions made during the measurement step.

12. A method according to claim 1, in which a plurality of average signals $Bf(i, t)$ are determined that relate to different points $r_0$ of the medium, and said mean signals $Bf(i, t)$ are used to build an image of the medium.

13. A method according to claim 1, in which the average signal $Bf(i, t)$ is used to compute a parameter that is specific to the medium.

14. A method according to claim 13, in which said parameter is the wave propagation speed.

15. A method according to claim 1, in which said waves are selected from among ultrasonic waves, mechanical waves, and electromagnetic waves.

16. Apparatus for of exploring by wave propagation, said apparatus comprising a set of transducers i suitable for emitting an incident wave into a diffusing medium, and for picking up signals representative of a reflected wave reverberated by the medium from the incident wave, the apparatus further comprising control means suitable for causing said set of transducers to take at least one measurement including a plurality of emissions (a1) during which the set of transducers i are caused to emit incident waves into the medium, and a plurality of receptions (a2) during which the signals representative of the reflected waves reverberated by the medium from each incident wave are picked up; and the device further comprising processing means adapted to performing a processing step (b) during which consideration is given to a plurality of sets k of reverberated signals $B_k(i, t)$, each of which comes substantially from a point $r_k$ belonging to the same isoplanatic zone $ZI(r_0)$ that is common to said sets k of signals and that itself relates to a point $r_0$ of the medium, the points $r_k$ being either different from one another regardless of the medium, or coinciding with the point $r_0$ when the medium includes diffusers having random motion;

said processing means being adapted to:
re-position in time the reverberated signals $B_k(i, t)$ of the sets k if the points $r_k$ are different from one another in order to obtain corrected signals $B0_k(i, t)=B_k(i, t-G_i(r_k))$, where the values $G_i(r_k)$ are delays such that, by causing the transducers i to emit signals $e_k(i, t)=e_0(i, t+G_i(r_k))$, the incident wave focuses substantially at the point $r_k$, the signals $e_0(i, t)$ being reference signals such that, by causing the transducers i to emit said reference signals $e_0(i, t)$, the incident wave focuses substantially at the point $r_0$; and to put into phase and average the signals $B0_k(i, t)=B_k(i, t-G_i(r_k))$ so as to obtain average signals $$Bf(i, t) = \sum_k A_k B0_k(i, t - c_k)$$

where the values $c_k$ are delays making it possible to put the signals $B0_k$ into phase, and the values $A_k$ are weighting coefficients.

* * * * *